US008911454B2

(12) United States Patent
Hayashi et al.

(10) Patent No.: US 8,911,454 B2
(45) Date of Patent: Dec. 16, 2014

(54) SUTURING DEVICE

(75) Inventors: Kensuke Hayashi, Yokohama (JP); Junji Shiono, Yokohama (JP)

(73) Assignee: Olympus Medical Systems Corp. (JP)

( * ) Notice: Subject to any disclaimer, the term of this patent is extended or adjusted under 35 U.S.C. 154(b) by 764 days.

(21) Appl. No.: 12/183,191

(22) Filed: Jul. 31, 2008

(65) Prior Publication Data

US 2010/0030236 A1 Feb. 4, 2010

(51) Int. Cl.
*A61B 17/04* (2006.01)
*A61B 17/00* (2006.01)
*A61B 17/29* (2006.01)

(52) U.S. Cl.
CPC ....... *A61B 17/0401* (2013.01); *A61B 17/00234* (2013.01); *A61B 17/0487* (2013.01); *A61B 2017/0034* (2013.01); *A61B 2017/00663* (2013.01); *A61B 2017/0409* (2013.01); *A61B 2017/0417* (2013.01); *A61B 2017/0488* (2013.01); *A61B 2017/2911* (2013.01); *A61B 2017/2946* (2013.01)
USPC .......................... 606/139; 606/144; 606/148

(58) Field of Classification Search
USPC ......... 606/139–148, 213, 232, 300, 205, 151, 606/916; 623/1.11; 600/104, 585
See application file for complete search history.

(56) References Cited

U.S. PATENT DOCUMENTS

| 5,425,743 A * | 6/1995 | Nicholas ....................... 606/208 |
| 5,549,617 A * | 8/1996 | Green et al. ................... 606/144 |
| 5,908,429 A * | 6/1999 | Yoon .............................. 606/144 |
| 6,066,146 A * | 5/2000 | Carroll et al. ................. 606/148 |
| 6,599,295 B1 * | 7/2003 | Tornier et al. ................. 606/104 |
| 2007/0073321 A1 * | 3/2007 | Mikkaichi et al. ............. 606/153 |
| 2007/0073322 A1 | 3/2007 | Mikkaichi et al. |
| 2007/0225754 A1 * | 9/2007 | Measamer et al. ............ 606/205 |
| 2008/0195144 A1 * | 8/2008 | Hashimoto .................... 606/205 |

FOREIGN PATENT DOCUMENTS

| EP | 1 913 879 A1 | 4/2008 |
| JP | 2001-501108 | 1/2001 |
| JP | 2004-000601 | 1/2004 |
| JP | 2006-239455 | 9/2006 |
| JP | 2007-044330 | 2/2007 |
| WO | WO 98/12991 | 4/1998 |
| WO | WO 2007/037326 A1 | 4/2007 |

OTHER PUBLICATIONS

Search Report issued by European Patent Office on Jan. 24, 2011 in connection with corresponding European patent application No. EP 09 00 9745.

(Continued)

*Primary Examiner* — Melanie Tyson
(74) *Attorney, Agent, or Firm* — Ostrolenk Faber LLP

(57) ABSTRACT

A suturing device that sutures tissues by releasing a suture unit includes: a first anchor and a second anchor included in the suture unit; a hollow needle receiving the first and second anchors inside of the needle; a tube which is fixed to a proximal end of the needle; a wire inserted into the tube and the needle; a first sheath through which the tube and the needle are inserted; an operating portion main body fixed to a proximal end of the first sheath; a slider fixed to a proximal end of the tube and configured to move forward and backward freely in a sliding manner with respect to the operating portion main body; a slider control portion configured to regulate movement of the slider with respect to the operating portion main body at all times; a handle portion provided in the slider; and a deactivation member.

3 Claims, 19 Drawing Sheets

(56) References Cited

OTHER PUBLICATIONS

Chinese Office Action mailed Jan. 14, 2011 in connection with corresponding Chinese Patent Application No. 200910160674.7.
English translation of Chinese Office Action issued in connection with corresponding Chinese application provided as an explanation of prior art relevancy.

Japanese Office Action mailed Jun. 18, 2013 in connection with corresponding Japanese Patent Application No. 2009-178237.
English translation of Japanese Office Action issued in connection with corresponding Japanese application provided as an explanation of prior art relevancy.

* cited by examiner

SUTURING DEVICE

BACKGROUND OF THE INVENTION

1. Field of the Invention

The present invention relates to a suturing device that is used by being inserted into a body cavity, and more particularly, to a suturing device that is used when suturing a perforation or the like formed in a lumen such as the stomach or the intestine with a suture thread having both ends fixed to an anchor.

2. Description of Related Art

In the past, for the purpose of suture of perforations, lacerations or the like formed in a lumen such as the stomach or the intestine, there has been known a suturing device that uses a suture thread having both ends fixed to an anchor (see WO 2007-37326, for example). In the suturing device, the anchors on both ends of the suture thread are placed to be locked at the tissues around the perforation at the inside or outside of the tissues, and the suture thread is pulled so that the tissues locked at the anchors are tightened, thereby suturing the tissues.

In the suturing device disclosed in WO 2007-37326, two anchors are fitted to the inside of a needle at the distal end of the suturing device. The proximal end of the needle is connected to a slider fitted to a main body so as to freely move in a sliding manner. By advancing and retracting the slider with respect to the main body, the protrusion length of the needle is varied. The anchor is released by relatively advancing a pusher inserted into the needle so as to freely advance and retract with respect to the needle.

SUMMARY OF THE INVENTION

According to a first aspect of the present invention, there is provided a suturing device that sutures tissues using a suture unit having a suture thread with ends fitted to a first anchor and a second anchor, respectively, the suturing device including: a hollow tip member receiving the first and second anchors; a wire having a front end inserted through the tip member so that the first and second anchors can be released from the tip member; a flexible tube having a distal end integrally connected to a proximal end portion of the tip member, through which the wire is inserted so as to freely move forward and backward in the axial direction of the tube; a main body fixed to a proximal end of a sheath through which the tube is inserted; and a sliding portion fixed to the proximal end of the tube and fitted to the main body so as to freely move with respect to the main body in the axial direction in a sliding manner, wherein the sliding portion includes a slider fixed to the proximal end of the tube, and a slider control portion which controls a sliding movement of the slider with respect to the main body in a normal state, and deactivates the control by a predetermined operation.

According to a second aspect of the present invention, there is provided a suturing device that sutures tissues using a suture unit having a suture thread with ends fitted to a first anchor and a second anchor, respectively, the suturing device including: a hollow tip member receiving the first and second anchors; a wire having a front end inserted through the tip member so that the first and second anchors can be released out from the tip member; a flexible tube having a distal end integrally connected to a proximal end portion of the tip member, through which the wire is inserted so as to freely move forward and backward in the axial direction of the tube; a main body fixed to a proximal end of a sheath through which the tube is inserted; and a sliding portion fixed to the proximal end of the tube and fitted to the main body so as to freely move in the axial direction of the main body in a sliding manner, wherein: the suture unit includes a stopper which has an insertion hole through which the suture thread is inserted, and controls a deviation of the suture thread with respect to the tissues sutured by the suture thread; and at the insertion hole, the end portion of the suture thread fitted to the first anchor is located to separate from the end portion of the suture thread fitted to the second anchor in the longitudinal direction of the stopper.

DESCRIPTION OF THE PREFERRED EMBODIMENTS

Hereinafter, a suturing device of one embodiment of the present invention will be described with reference to FIGS. 1 to 20.

Figure 1:
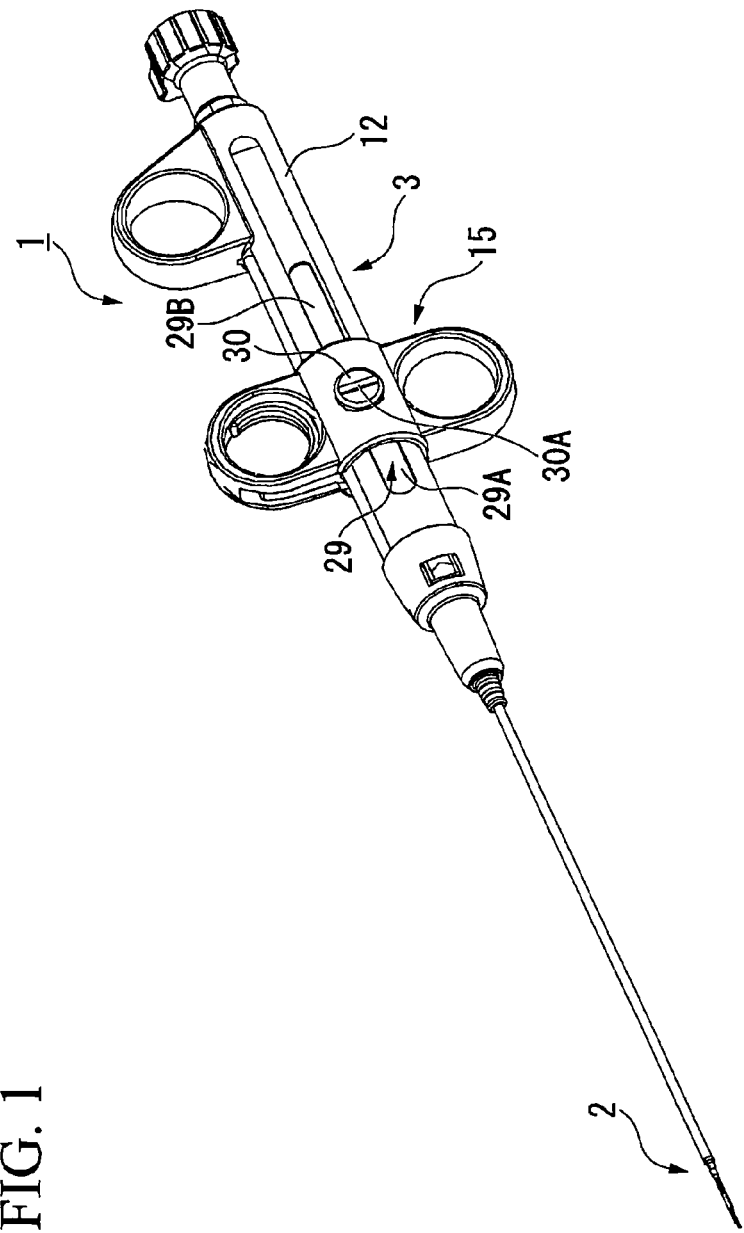
FIG. 1 is a perspective view of a suturing device of one embodiment of the present invention.

FIG. 1 shows a suturing device 1 of the present embodiment. The suturing device 1 is an endoscopic treatment tool for suturing tissues within the body cavity by releasing a suture unit (described below). The suturing device 1 is configured to include a distal end portion 2 that is inserted into the body, and an operating portion 3 for operating various mechanisms installed in the distal end portion 2.

Figure 2:
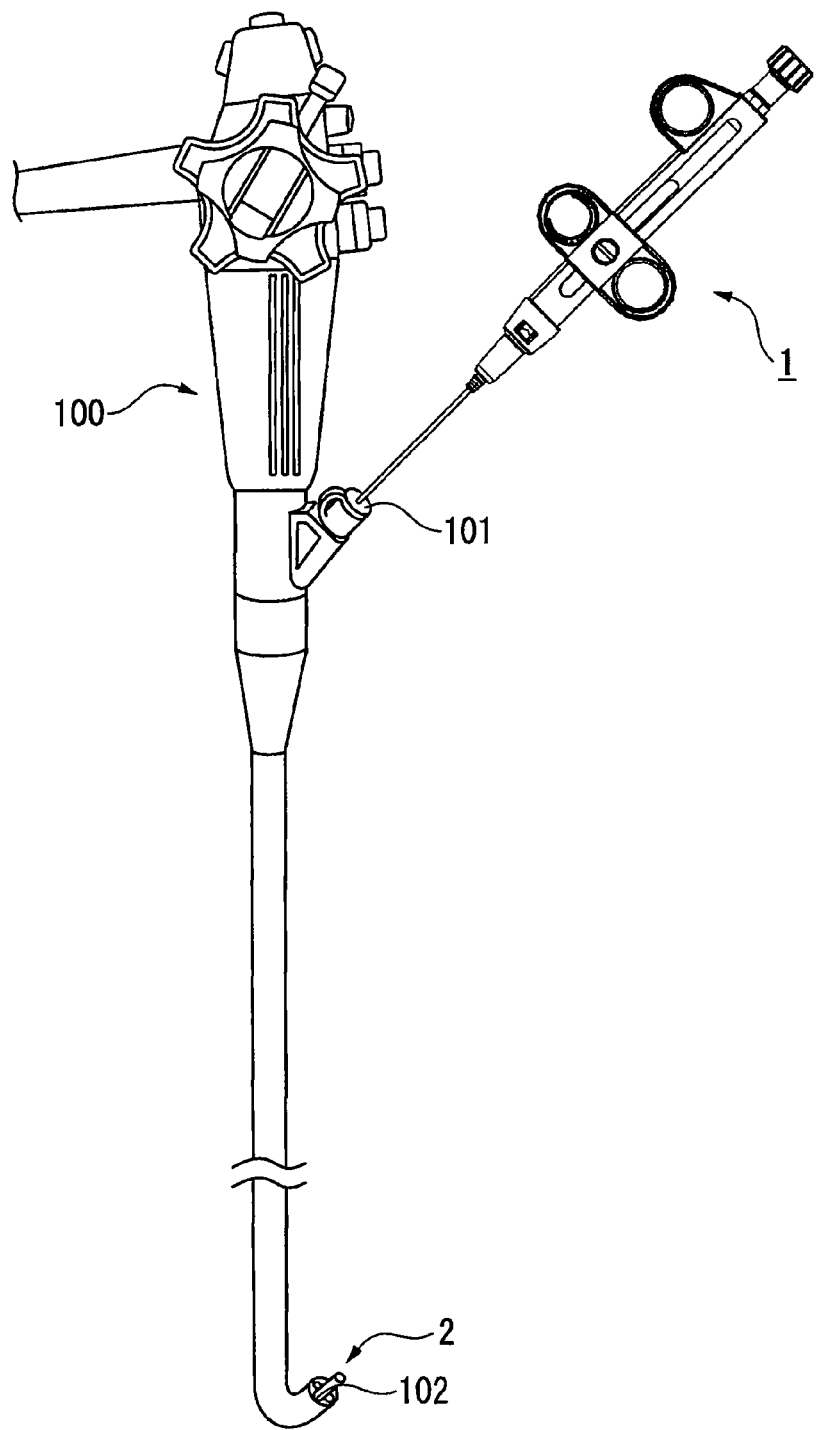
FIG. 2 shows the state in which the suturing device is inserted into an endoscope.

As shown in FIG. 2, the suturing device 1 is used by being inserted into a forceps channel 101 of an endoscope 100 and making a distal end thereof protrude out from an endoscope channel 102 inside the body cavity of a patient or the like.

Figure 3:
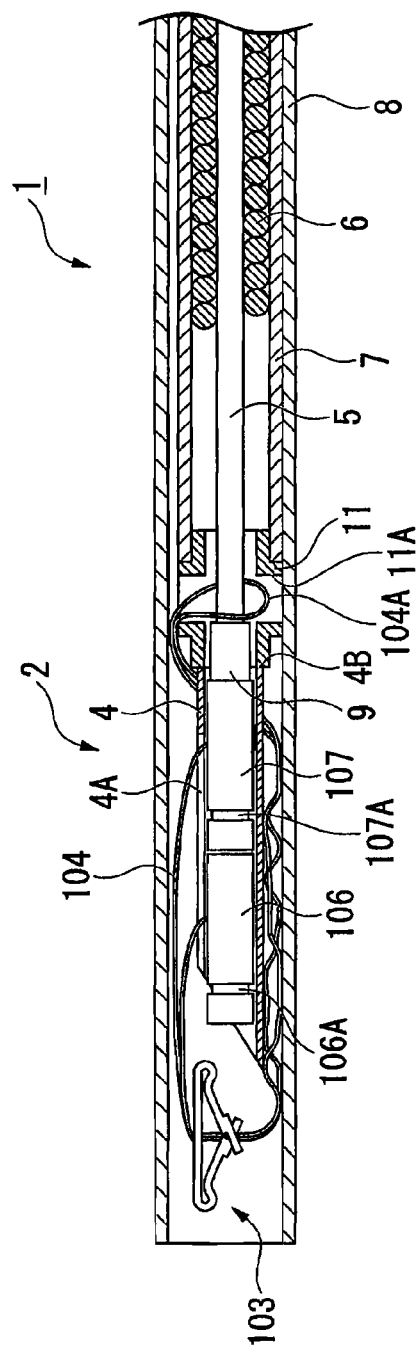
FIG. 3 is an enlarged sectional view of a distal end portion of the suturing device.

FIG. 3 is an enlarged sectional view of the distal end portion 2. The distal end portion 2 is configured to include a needle (a tip member) 4 that is fitted to the suture unit, a wire 5 that is inserted into the needle 4, a second sheath 6 into which the proximal end of the wire 5 is inserted, a tube 7 through which the second sheath 6 and the wire 5 are inserted so as to freely advance and retract in the axial direction of the tube 7 and which is integrally fixed to the needle 4 at the proximal end side, and a first sheath (a sheath) 8 through which the tube 7 is inserted.

The needle 4 is a hollow member made of metal or the like, and a groove 4A is formed on the top surface thereof. Anchors of the suture unit are received in the inside of the needle 4.

Figure 4:
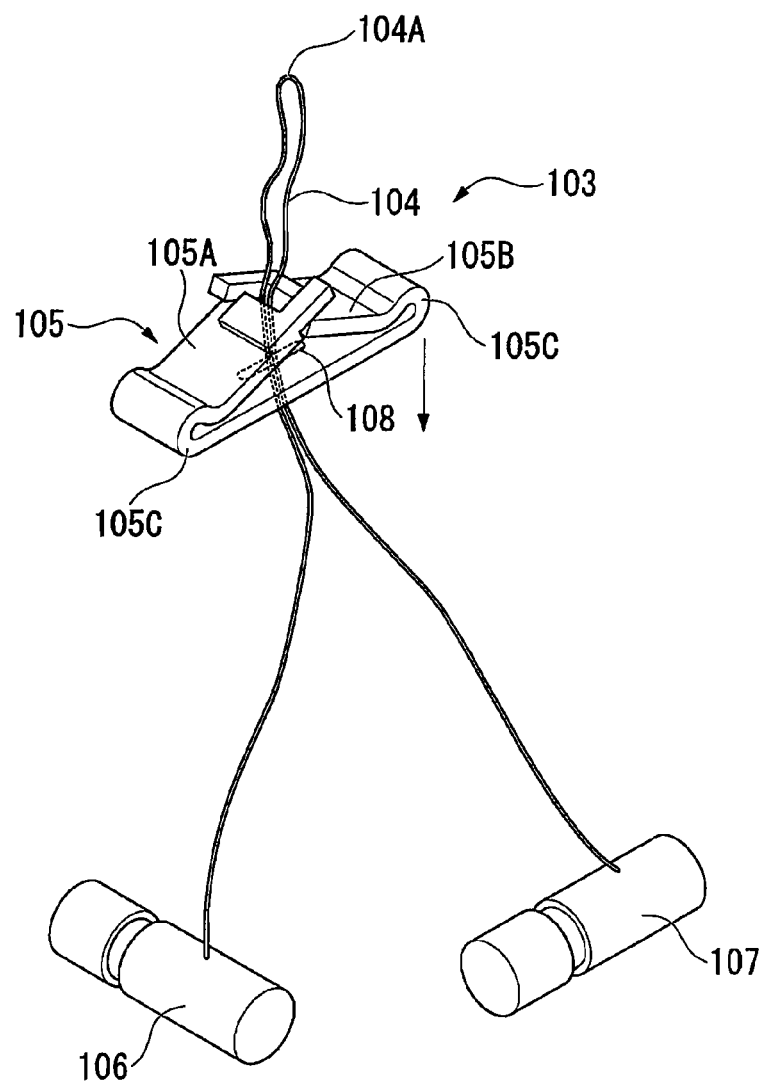
FIG. 4 shows a suture unit that is used in the suturing device.

FIG. 4 is a diagram showing the suture unit 103 that is received in the needle 4. The suture unit 103 is configured to include a suture thread 104, a stopper 105 through which the suture thread 104 is inserted, and first and second rod-shaped anchors 106 and 107 that are fitted to both ends of the suture thread 104.

The stopper 105 is a plate-shaped member made of metal or resin such as a biodegradable resin. The stopper 105 is folded so that left and right end portions 105A and 105B are opposed to each other and are engaged with each other. Folded portions 105C of the end portions 105A and 105B are formed in a so-called hair pin shape such that the plate-shaped member does not make a shape angle at the folded portions 105C. This makes it possible to prevent a concentration of stress at the folded portions, thereby preventing the occurrence of a crack or the like.

An insertion hole 108 having art elliptical shape extending in the longitudinal direction of the stopper 105 is provided at the substantially central portion in the longitudinal direction of the stopper 105. The suture thread 104 is folded at a mid-point portion 104A, and the suture thread 104 is inserted through the insertion hole 108 from the opposite surface of the end portions 105A and 105B so as to pass between the end portions 105A and 105B that are engaged with each other. Operations of the stopper 105 in the operating state will be described later.

As shown in FIG. 3, the first and second anchors 106 and 107 of the suture unit 103 are received in the inside of the needle 4 in a state where the first and second anchors 106 and 107 are linearly aligned in the axial direction with the first anchor 106 disposed at the more distal end side. The suture thread 104 connected to the anchors 106 and 107 are exposed from the groove 4A to the outside of the needle 4.

Incidentally, engagement grooves 106A and 107A are formed on the entire circumference at a portion of the outer surface of each of the first and second anchors 106 and 107, respectively. Each of the engagement grooves 106A and 107A engages with an engagement protrusion (not shown) that is provided on the inner cavity of the needle 4, thereby preventing erroneous release of the anchors 106 and 107 or natural separation thereof when the distal end of the needle 4 is perpendicularly held to face downward.

The wire 5 is formed of metal or the like, and a distal end thereof is inserted through the needle 4 from the proximal end 43 of the needle 4. A pressing member 9 is mounted at the distal end of the wire 5. When the wire 5 is moved in the forward direction in the axial direction toward the distal end of the wire 4, the pressing member 9 is pressed against the first and second anchors 106 and 107, thereby allowing the anchors 106 and 107 to be released from the needle 4.

The wire 5 is preferably a single wire that can transfer the pressing force applied from the operating portion 3 to the pressing member 9 in an appropriate manner. However, a multi-line wire obtained by twisting a number of metallic strands, a coil wire obtained by winding a number of metallic strands or a multi-line wire in a coil, or other wires may be used.

The second sheath 6 is a coil sheath formed by winding metal strands or multi-line wires in a tubular shape, and the proximal end of the wire 5 is inserted through the second sheath so as to freely advance and retract in the axial direction.

The tube 7 is a flexible, tubular member made of resin or the like. As a material for the tube 7, a material such as resin that has a small expansion ratio in the axial direction is preferred. The tube 7 is integrally connected to the proximal end 4B of the needle 4 via a connection tube 11 that is mounted on the distal end of the tube 7.

A through-hole 11A (connection portion) is formed on the outer surface of the connection tube 11 so as to be penetrated through the inner cavity of the connection tube 11. The folded mid-point portion 104A of the suture thread 104 of the suture unit 103 is inserted through the through-hole 11A into the inner cavity of the connection tube 11 and is tied to the wire 5 inserted into the inner cavity. The inner diameter of the connection tube 11 in the axial direction is set smaller than the outer diameter of the second sheath 6, and the second sheath 6 cannot enter the connection tube 11.

The first sheath 8 is a coil sheath having the same structure as the second sheath 6. The tube 7 and the needle 4 which is integrally connected to the tube 7 are inserted through the first sheath 8 so as to freely advance and retract in the axial direction. As shown in FIG. 3, the entire suture unit 103 fitted to the needle 4 can be received in the inside of the first sheath 8.

Figure 5:
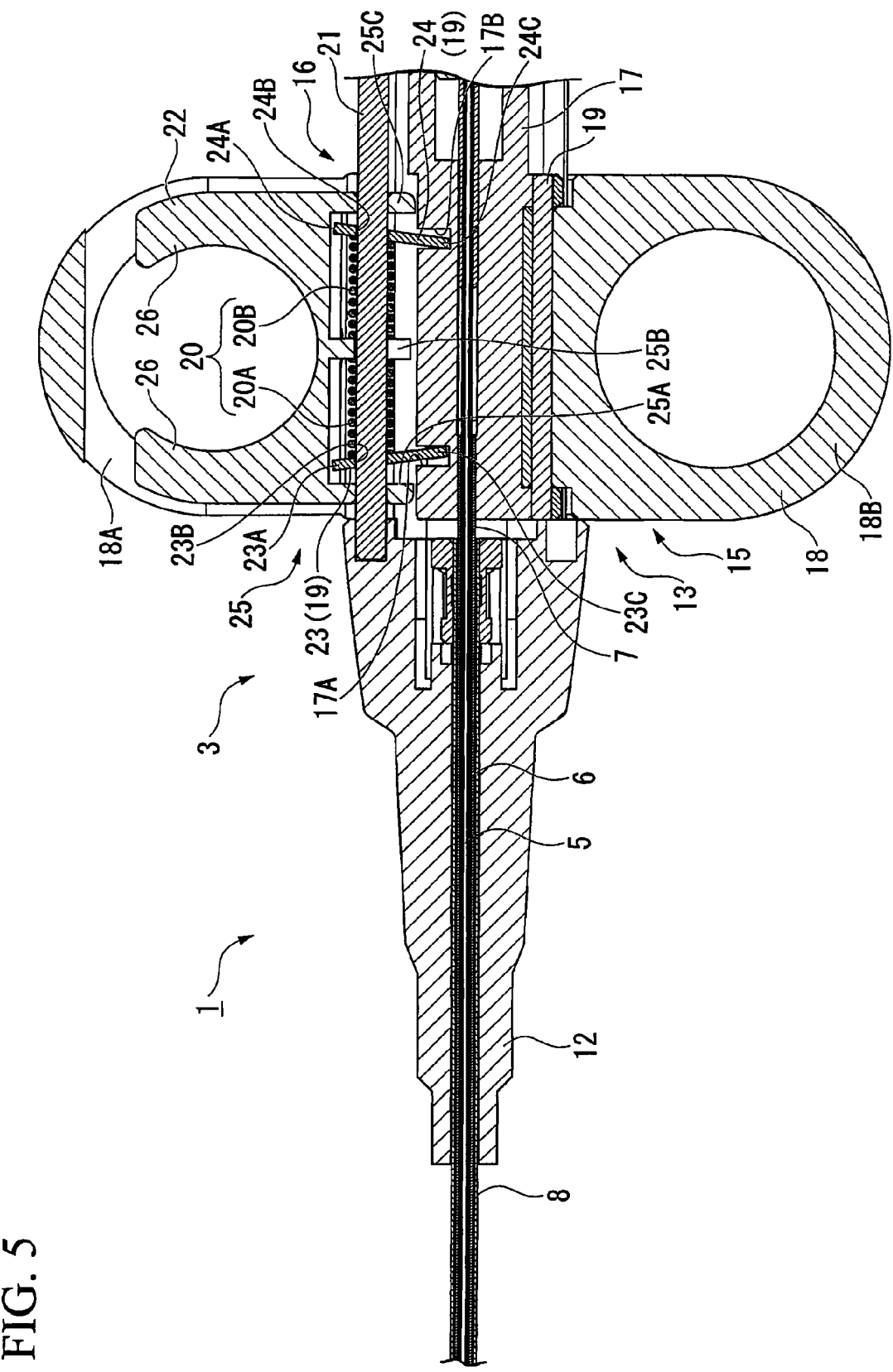
FIG. 5 is a sectional view of a distal end portion of an operating portion of the suturing device.
Figure 6:
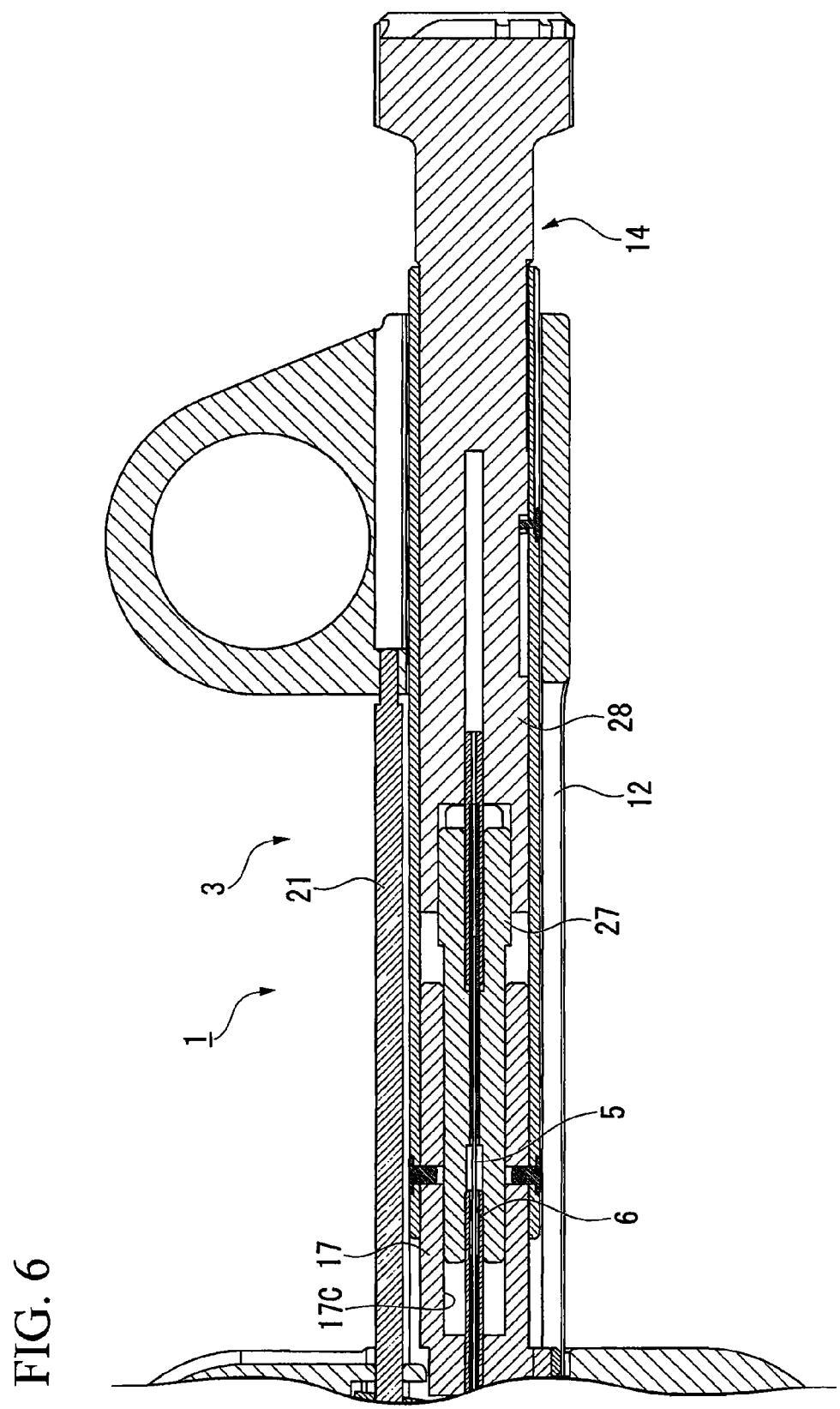
FIG. 6 is a sectional view of a proximal end portion of the operating portion.

FIG. 5 is a sectional view of the distal end portion of the operating portion 3. FIG. 6 is a sectional view of the proximal end portion of the operating portion 3. As shown in FIGS. 5 and 6, the operating portion 3 is provided at the proximal end of the wire 5 and the second sheath 6 and is configured to include an operating portion main body 12 fixed to the proximal end of the first sheath 8, a sliding portion 13 fitted to the operating portion main body 12 so as freely move in the axial direction of the operating portion main body 12 in a sliding manner, and a release portion 14.

The operating portion main body 12 is made of resin or the like and formed in a substantially tubular shape. A space for allowing the wire 5 and the second sheath 6 to pass therethrough is provided inside the operating portion main body 12 so as to extend in the axial direction. The proximal end 8A of the first sheath 8 is fixed to the distal end of the operating portion main body 12 by means of an adhesive bonding, a caulking, or the like.

The sliding portion 13 is configured to include a slider 15 fitted to the operating portion main body 12 so as to freely move in a sliding manner, and a slider control portion 16 for controlling the sliding movement of the slider 15.

The slider 15 is provided with a slider main body 11 which is capable of moving inside the operating portion main body 12 in the axial direction in a sliding manner and a handle portion 18 which is integrally fitted to the slider main body 17. The proximal end of the tube 7 is connected to the slider main body 17. When the slider main body 17 moves in the axial direction of the operating portion main body 12 in a sliding manner, the tube 7 and the needle 4 move in a sliding manner accompanying with the slider main body 17.

The handle portion 18 is formed so as to surround the main body and is integrally fixed to the slider main body 17 via a fixing shaft 19. Rings 18A and 18B for hooking fingers are provided in the handle portion 18. The user moves the slider 15 with respect to the operating portion main body 12 in a sliding manner by hooking fingers into the rings 18A and 18B.

The slider control position 16 is configured to include a pair of plate clutches 19 which are disposed between the slider main body 17 and the handle portion 18, a pair of biasing members 20 which bias the plate clutches 19, respectively, a shaft 21 which is inserted through the plate clutches 19 and the biasing members 20, and a lever 22 (deactivation member) for deactivating a control of a sliding movement by the plate clutch 19.

The pair of the plate clutches 19 includes a first clutch 23 of the distal end side and a second clutch 24 of the proximal end side. In the first and second clutches, through-holes 23B and 24B are formed in first end portions 23A and 24A at the ring 18A side, respectively. The diameter of each of the through-holes 23B and 24B is set greater than the diameter of the shaft 21 inserted therethrough. On the other hand, grooves 17A and 17B are formed in the slider main body 17 so that the grooves are substantially orthogonal to the axial direction of the slider main body 17, and second end portions 23C and 24C which are opposite to the slider main body 17 are inserted into the grooves 17A and 17B. The length of each of the grooves 17A and 17B in the axial direction of the slider main body 17 is set greater than the thickness of each of the clutches 23 and 24.

The biasing members 20 include a first biasing member 20A of the distal end side and a second biasing member 20B of the proximal end side, and are disposed between the first clutch 23 and the second clutch 24 in a state in which the shaft 21 is inserted through the biasing members. Each end of the biasing members 20A and 20B abuts a second partition wall 25B of the lever 22 such that the first biasing member 20A biases the first end portion 23A of the first clutch 23 toward the distal end and that the second biasing member 20B biases the first end portion 24A of the second clutch 24 toward the proximal end.

That is, the first end portions 23A and 24A are biased by the pair of the biasing members 20 so as to separate from each other in the advancing and retracting direction of the slider 15. The second end portions 23C and 24C of the pair of the plate clutches 19 are positioned between the first end portions 23A and 24A in the advancing and retracting direction of the slider 15 in the normal state where the user does not operate the slider 15 such that the clutches form a truncated chevron shape as shown in FIG. 5.

Note that, a spring can be favorably adopted as the biasing member 20, and other elastic member such as rubber may be adopted.

The shaft 21 has a rod shape, and the distal end of the shaft 21 is fixed to the operating portion main body 12. The shaft 21 is inserted through the handle portion 18 of the slider 15 and moreover inserted through the plate clutches 19, the biasing members 20, and the lever 22 inside the handle portion 18.

The lever 22 includes a partition wall portion 25 having a through-hole, and a pressing portion 26 which is pressed when the user deactivates a control by the slider control portion 16.

The partition wall portion 25 includes a first partition wall 25A (abutting portion) of the distal end side, the second partition wall 25B of the middle, and a third partition wall 25C (abutting portion) of the proximal end side. Each of the partition walls has a through-hole having a diameter substantially equal to the diameter of the shaft 21. The shaft 21 is inserted through and fixed to the first, second and third partition walls 25A, 25B and 25C in a state where the first partition wall 25A is positioned closer to the distal end than the first clutch 23, the second partition wall 25B is positioned between the first and second biasing members 20A and 20B, and the third partition wall 25C is positioned closer to the proximal end than the second clutch 24.

The pressing portion 26 is formed such that portions of the pressing portion 26 protrude to the inside of the ring 18 toward the distal end and the proximal end, respectively, in the normal state. Although the inner circumference of the pressing portion is formed in a substantially arc shape in the present embodiment, the shape thereof is not particularly limited. When the user hooks their fingers into the ring 18A to press the ring 18A toward the distal end or proximal end, the lever 22 is moved in a sliding manner toward the distal end or proximal end along the shaft 21.

As shown in FIG. 6, the release portion 14 for releasing out the suture unit 103 is configured to include a first rod 27 which is connected to the proximal ends of the wire 5 and the second sheath 6, and a second rod 28 which is connected to the first rod 27.

The distal end of the first rod 27 is inserted into a hole 17C provided in the proximal end of the slider main body 17 and is connected and fixed to the proximal ends of the wire 5 and the second sheath 6 which extend through the slider main body 17 by means of a brazing, an adhesive bonding, or the like. The first rod 27 freely advances and retracts in the axial direction with respect to the operating portion main body 12 and the slider main body 17.

The second rod 28 is inserted into the operating main body 12 from the proximal end of the operating portion main body 12. The distal end portion of the second rod 28 is connected and fixed to the proximal end of the first rod 27. The proximal end portion of the second rod 28 is enlarged in diameter to form a button shape in order to make the operation by the user easier.

The second rod 28 is formed so as to freely advance and retract in the axial direction with respect to the operating portion main body 12. Therefore, when advancing and retracting the second rod 28 in the axial direction, it is possible for the first rod 27, the wire 5, the second sheath 6, and the pressing member 9 to advance and retract.

Furthermore, as shown in FIG. 1, a groove 29 is provided on the outer circumference surface of the operating portion main body 12 so as to extend in the direction of the operating portion main body. In the groove 29, a width of a first region 29 of the distal end side is set greater than a width of a second region 29B of the proximal end side. A screw 30 is screwed into the slider 15 such that a shaft of the screw 30 penetrates the slider 15 to be engaged with the groove 29, thereby preventing an erroneous movement of the sliding portion 13. An index line 30A showing the orientation of the shaft is provided in the screw 30. The way of preventing an erroneous movement of the sliding portion 13 by the groove 29 and the screw 30 will be described later.

Hereinafter, operations of the thus-constructed suturing device 1 in the operating state will be described.

First, the endoscope 100 is inserted into the body cavity of a patient or the like, and the distal end of the endoscope 100 is moved to the vicinity of a tissue as a treatment target such as a perforation or the like.

Next, as shown in FIG. 2, the distal end of the suturing device 1 is inserted into the forceps channel 101, and the distal end portion 2 of the suturing device 1 is exposed to the outside from the endoscope channel 102.

Figure 7A:
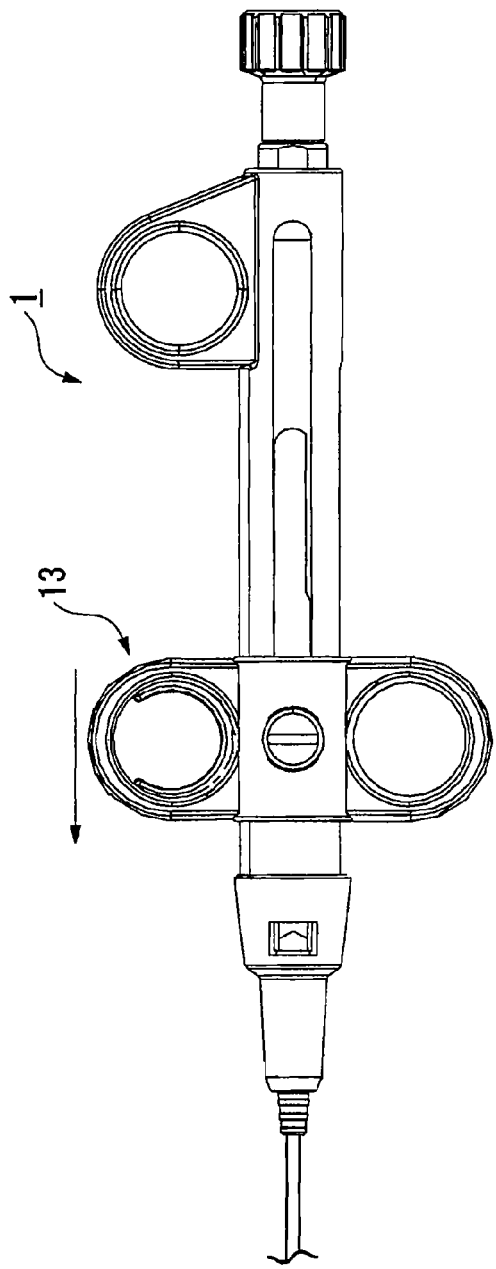
FIG. 7A shows a movement of a sliding portion at the time of operating the suturing device.
Figure 7B:
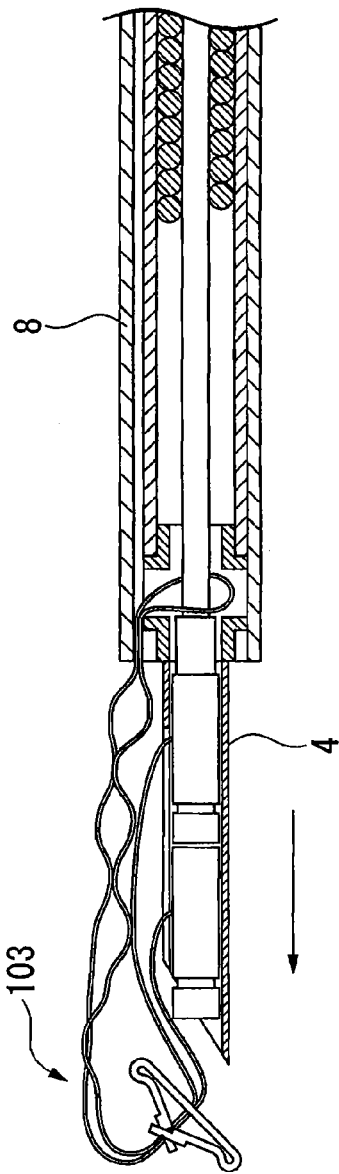
FIG. 7B is an enlarged sectional view showing a movement of the distal end portion in the operating state.

The user moves the slider 13 in the forward direction in a sliding manner, as shown in FIG. 7A. Then, as shown in FIG. 7B, the needle 4 and the suture unit 103 fitted to the needle 4 are exposed from the distal end of the first sheath 8.

Figure 8:
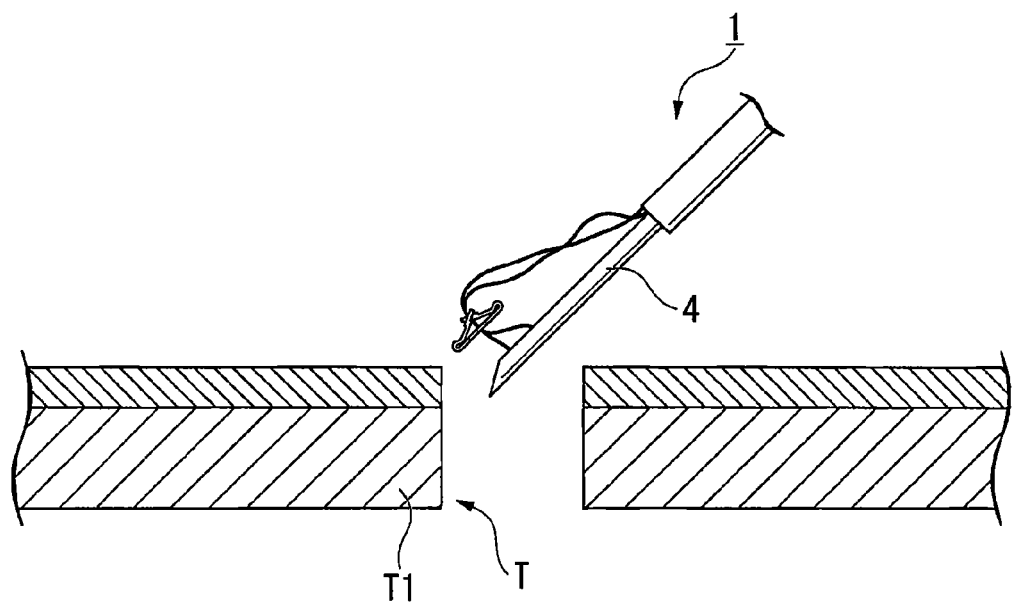
FIG. 8 shows the state in which the suturing device is inserted into a target tissue.

Then, as shown in FIG. 8, in a state that the needle 4 is protruded out, the user moves the distal end of the suturing device 1 to the vicinity of a target tissue T around a perforation or the like and inserts the needle 4 into a tissue T1 so as to penetrate through the tissue T1.

In the state that the needle 4 is penetrated through the tissue T1, the user pushes the second rod 28 of the release portion 14 to advance the second rod 28 with respect to the operating portion main body 12. Then, the second sheath 6 and the wire 5 are moved in the forward direction in a sliding manner. Since the second sheath 6 is a coil sheath, the second sheath 6 has adequate strength against compression in the axial direction. As a result, the pressing operation of the second rod 28 is suitably transmitted to the second sheath 6 and the wire 5, thereby enabling to advance the second sheath 6 and the wire 5.

Figure 9:
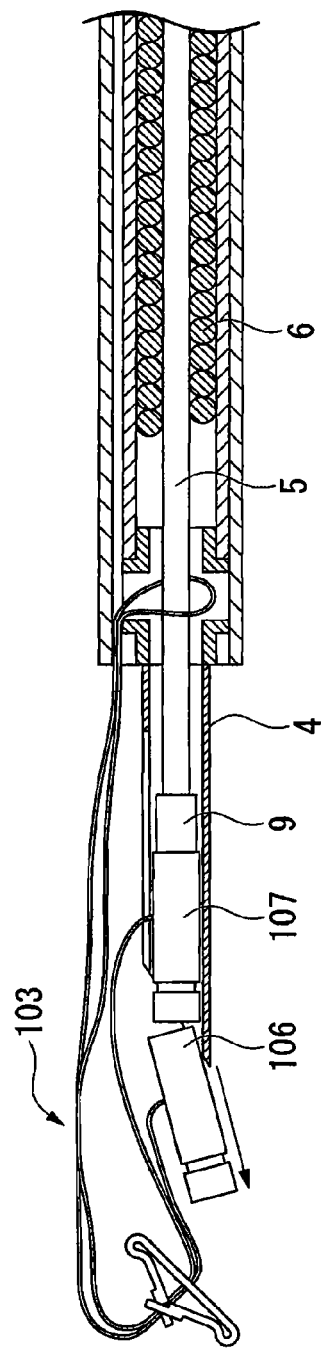
FIG. 9 is an enlarged sectional view of a distal end portion of the suturing device in the operating state.
Figure 10:
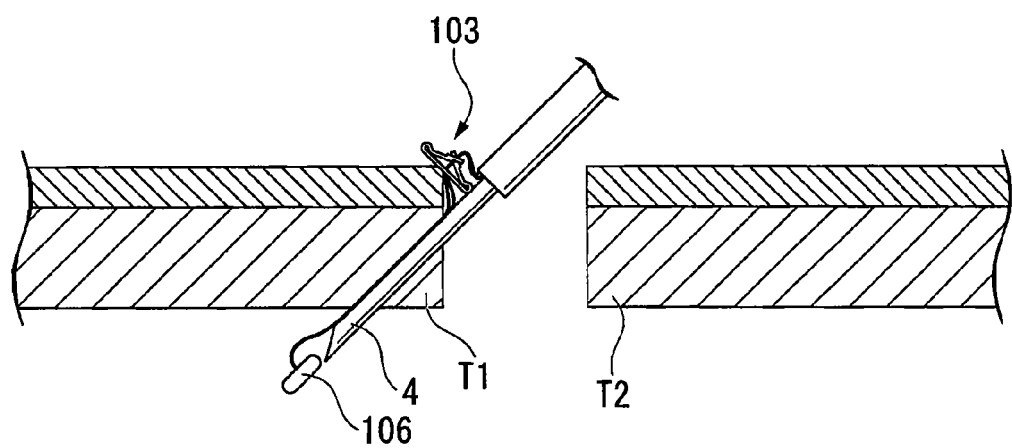
FIG. 10 shows a step of a suturing operation by the suturing device.

When the user pushes the second rod 28 to a predetermined amount, as shown in FIGS. 9 and 10, the first and second anchors 106 and 107 of the suture unit 103 are pushed by the pressing member 9 at the distal end of the wire 5 to move forward, thereby allowing the first anchor 106 at the distal end side to be released out from the needle 4.

Then, the user pulls out the needle 4 from the tissue T1. At this time, the first anchor 106 remains locked at the tissue T1. After this, the needle 4 is inserted into a tissue T2 opposite the tissue T1 with the perforation or the like disposed therebetween so as to penetrate through the tissue T2.

Figure 11:
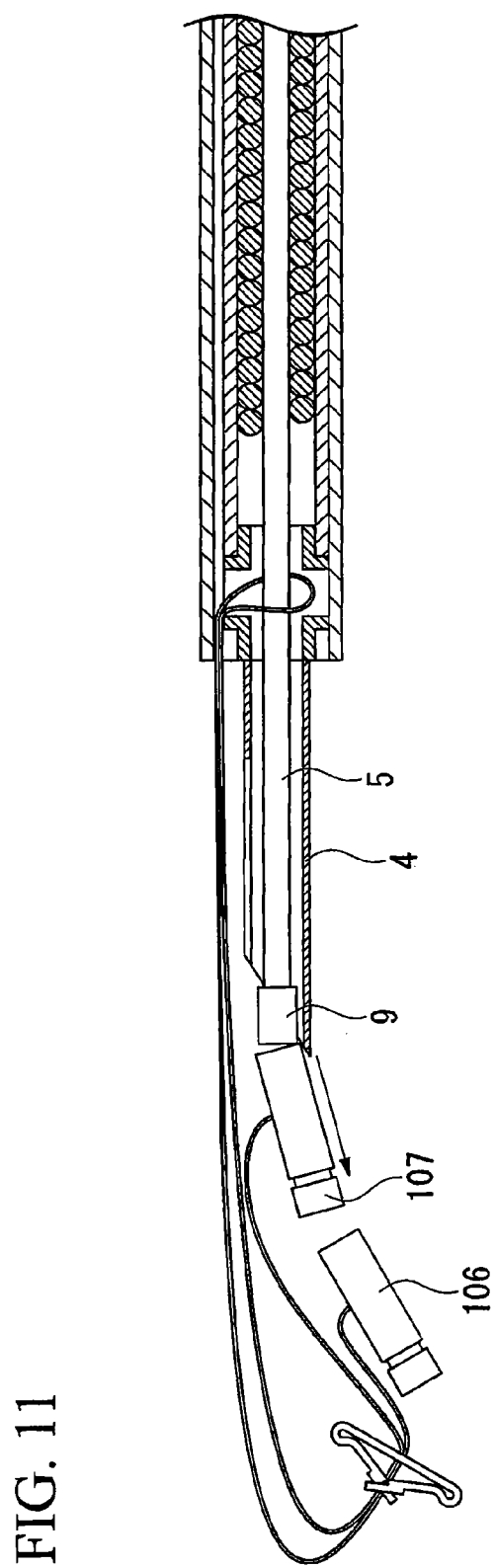
FIG. 11 is an enlarged sectional view of a distal end portion of the suturing device in the operating state.
Figure 12:
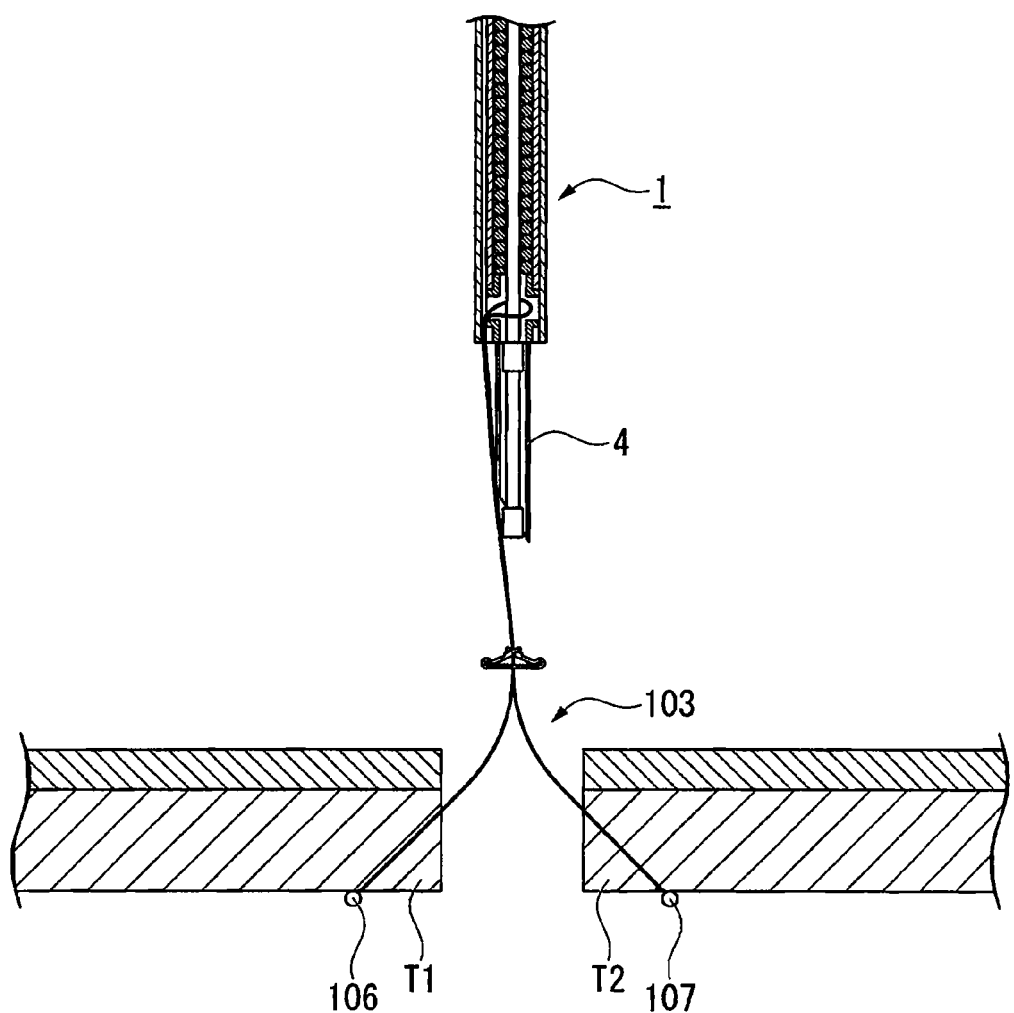
FIG. 12 shows a step of a suturing operation by the suturing device.

After penetrating the needle 4 through the tissue T2, when the user further pushes the second rod 28 by a predetermined amount, as shown in FIG. 11, the wire 5 is further moved forward, thereby allowing the second anchor 107 to be released from the needle 4. After the second anchor 107 is released, as shown in FIG. 12, the user pulls out the needle 4 from the tissue T2, while leaving the second anchor 107 locked at the tissue T2.

If the slider 15 advances and retracts at the time of the above-described releasing operation of the first and second anchors 106 and 107, the protrusion-length of the needle 4 is varied. Therefore, there is a possibility of the release of the anchors 106 and 107 becoming difficult. However, in the suturing device 1, since the slider control portion 16 controls an undesired movement of the slider 15 in the forward and backward direction, it is possible to perform the release operation securely. Detailed explanation will be described below.

Figure 13:
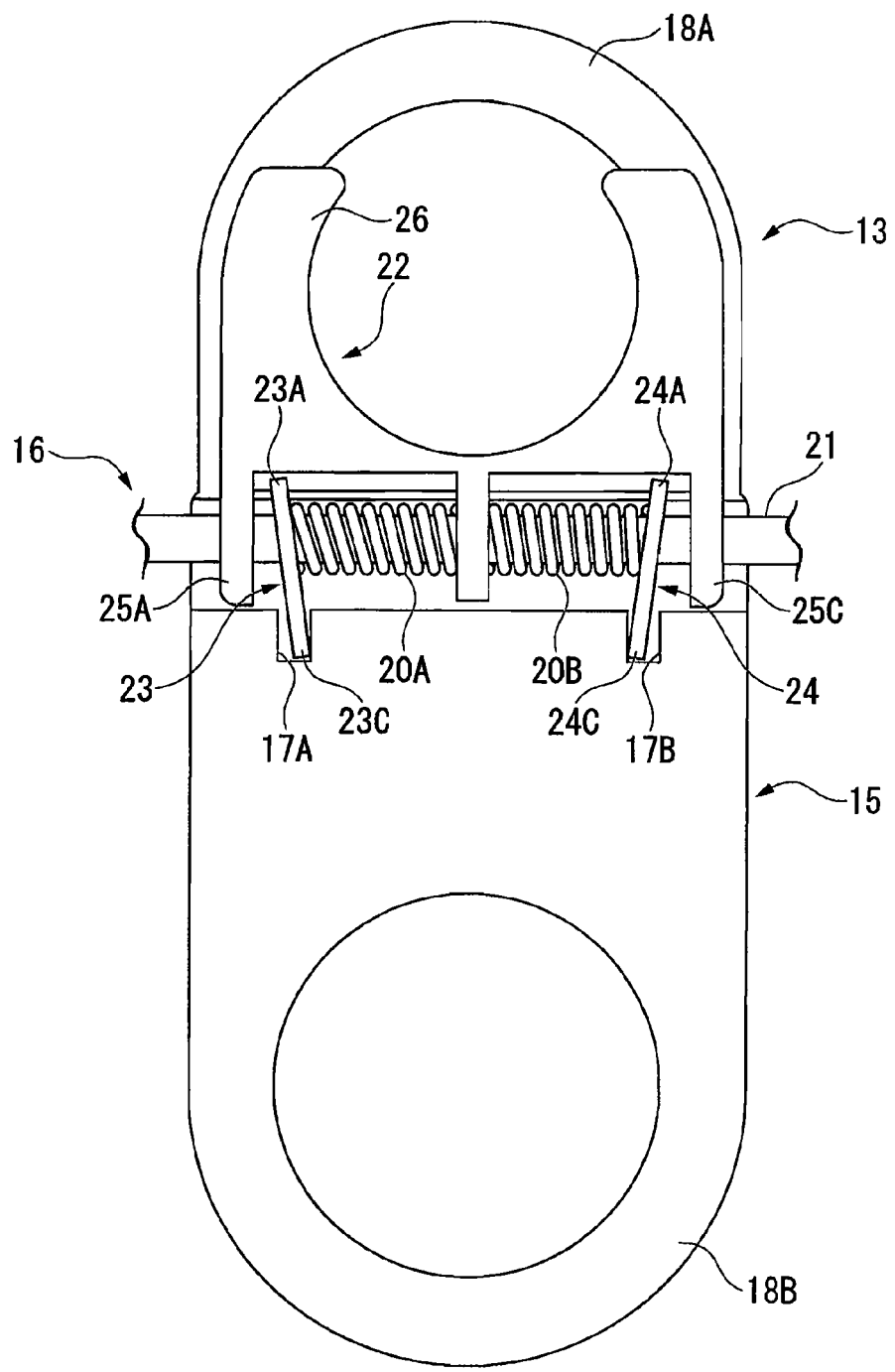
FIG. 13 shows a slider control portion of the suturing device in the normal state.

FIG. 13 shows the sliding portion 13 in the normal state where the user does not operate the sliding portion 13. Note that the grooves 17A and 17B of the slider main body 17 and the handle portion 18 are described as a unit in FIG. 13 in order to simplify the figure. As described above, the first end portions 23A and 24A of the clutches 23 and 24 are biased by the biasing members 20A and 20B, respectively, so that the first end portions are separated from each other in the axial direction of the sliding portion 13.

Therefore, when the slider 15 attempts to advance, the second end portion 24C of the second clutch 24 is pushed toward the distal end by the groove 17B of the slider main body 17. As a result, since the second clutch 24 serves as a physical obstruction such that the second clutch 24 is slanted and is jammed between the groove 17B and a space between the second biasing member 20B and the third partition wall 25C, thereby preventing the slider 15 from moving on the shaft 21 in a sliding manner. As a result, the movement of the sliding portion 13 toward the distal end is restricted.

Similarly, when a tendency for the slider 15 to be retracted arises, the second end portion 23C of the first clutch 23 is pushed toward the proximal end by the groove 17A of the slider main body 17. As a result, the first clutch 23 is slanted and is jammed between the groove 17A and a space between the first biasing member 20A and the first partition wall 25A, thereby restricting the movement of the sliding portion 13 toward the proximal end. That is, in the normal state, the sliding portion 13 is held by the slider control portion 16 in a state where the sliding portion 13 is not allowed to advance and retract with respect to the operating portion main body 12.

When advancing the slider 15, the user hooks their fingers into the rings 18A and 18 to push the slider 15 forward (i.e., toward the distal end). By operating thus the distal end portion of the pressing portion 26 of the lever 22 which protrudes to the inside of the ring 18A is pressed.

Figure 14:
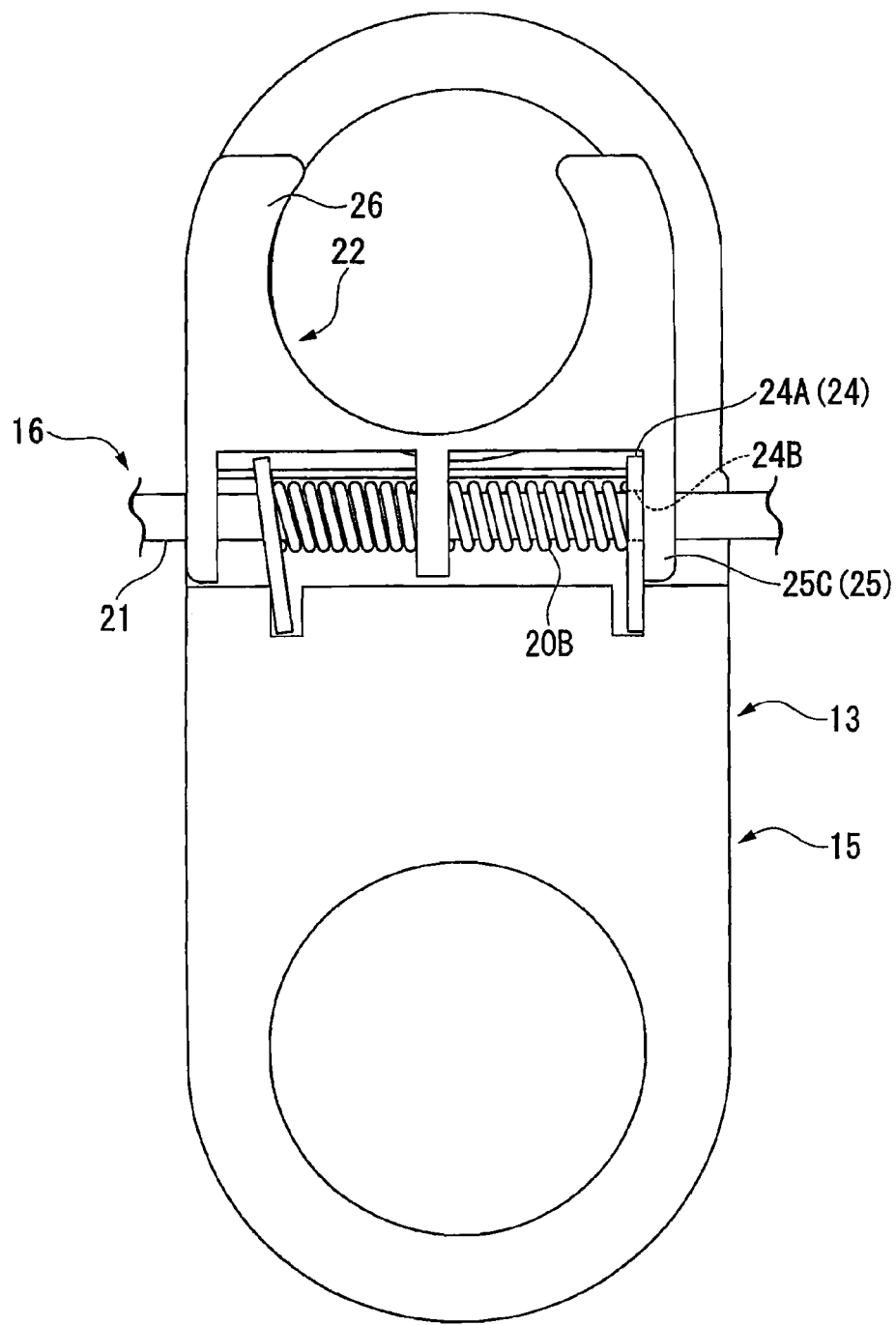
FIG. 14 shows the slider control portion when a control of a sliding movement toward the distal end is deactivated.

Then, as shown in FIG. 14, the lever 22 moves forward with respect to the shaft 21 such that the third partition wall 25C of the partition wall portion 25 pushes the first end portion 24A of the second clutch 24 in the forward direction against the biasing force of the second biasing member 20B. As a result, the angle between the second clutch 24 and the shaft 21 changes to be substantially a right-angle. Since the diameter of the through-hole 24B of the second clutch 24 is set greater than the diameter of the shaft 21, when the second clutch 24 and the shaft 21 are orthogonal to each other, a gap (not shown) occurs between the through-hole 24B and the shaft 21. As a result, it becomes possible for the slider 15 to move on the shaft 21 in a sliding manner, thereby deactivating the control by the slider control portion 16.

Figure 15:
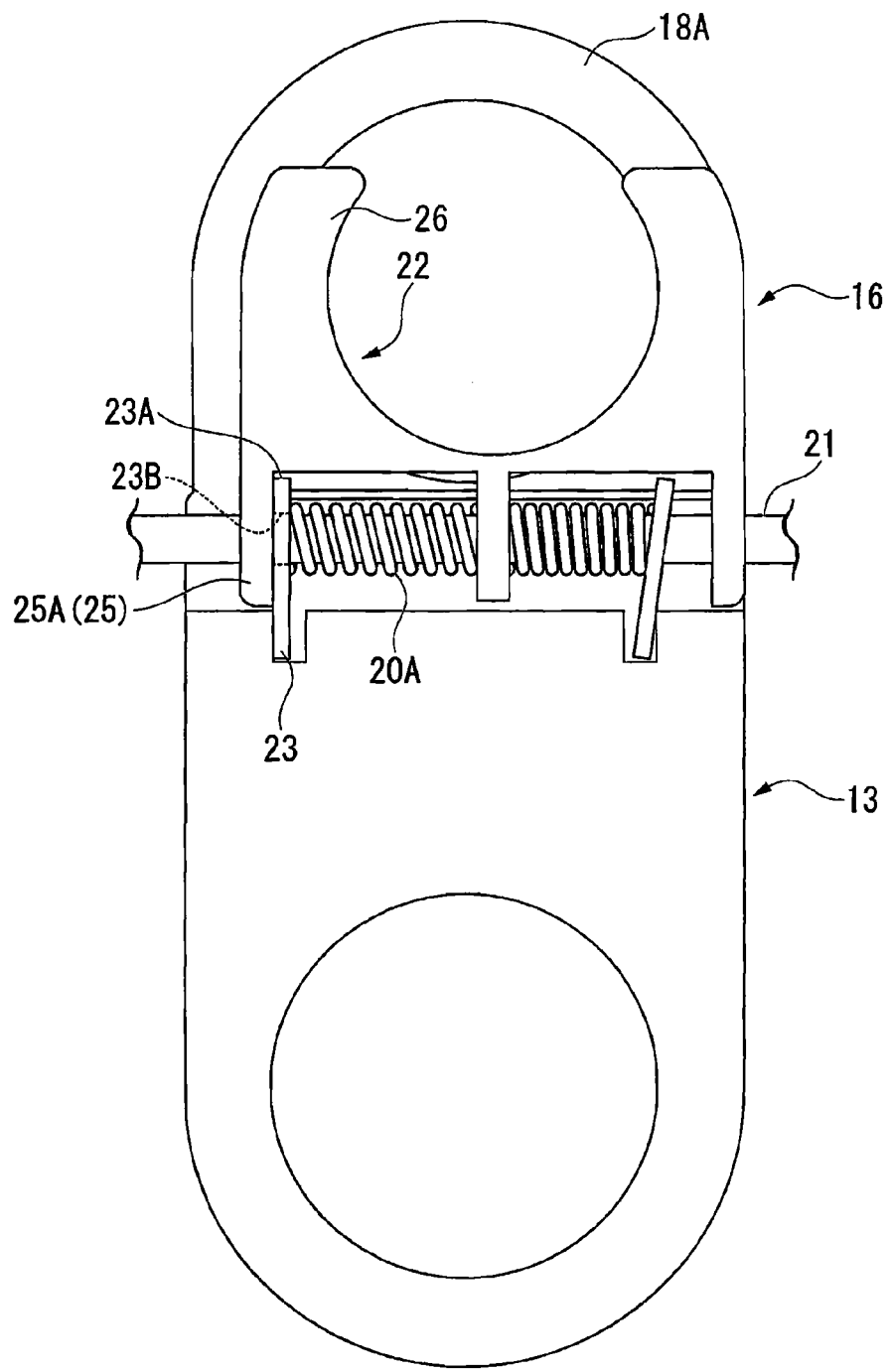
FIG. 15 shows the slider control portion when a control of a sliding movement toward the proximal end is deactivated.

Similarly, when retracting the slider 15, as shown in FIG. 15, the proximal end portion of the pressing portion 26 is pressed such that the first clutch 23 and the shaft 21 become orthogonal to each other. Therefore, the control by the slider control portion 16 is deactivated.

After locking the anchors 106 and 107 to the tissues, the user retracts the slider 15 with respect to the operating portion main body 12 such that the tube 7 and the needle 4 is received in the first sheath 8. At this time, since the second rod 27 is retracted along with the slider 15, the wire 5 and the second sheath 6 is also retracted.

Figure 16:
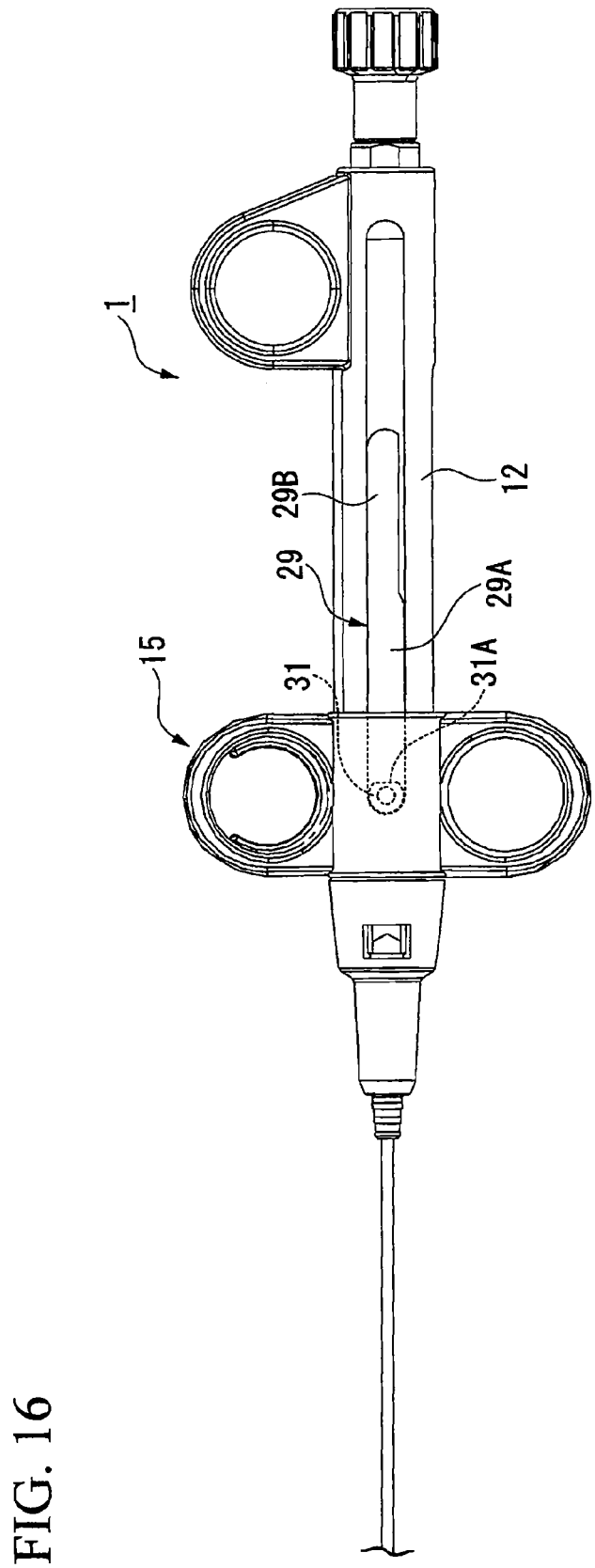
FIG. 16 shows the state in which a slidably movable range of a sliding portion of the suturing device is limited within a first region of a groove.

At this time, when the index line 30A of the screw 30 is substantially orthogonal to the axial direction of the slider 15 as shown in FIG. 1, a shaft 31 of the screw 30 formed in a so-called D-shape having a flat portion 31A is disposed such that the flat portion 31A is substantially parallel to the width direction of the groove 29 formed in the operating portion main body 12 as shown in FIG. 16. As a result, the shaft 31 is not allowed to enter the second region 29B of the groove 29 having a narrower width and the slidably movable range of the slider 15 is restricted within the first region 29A.

Figure 17:
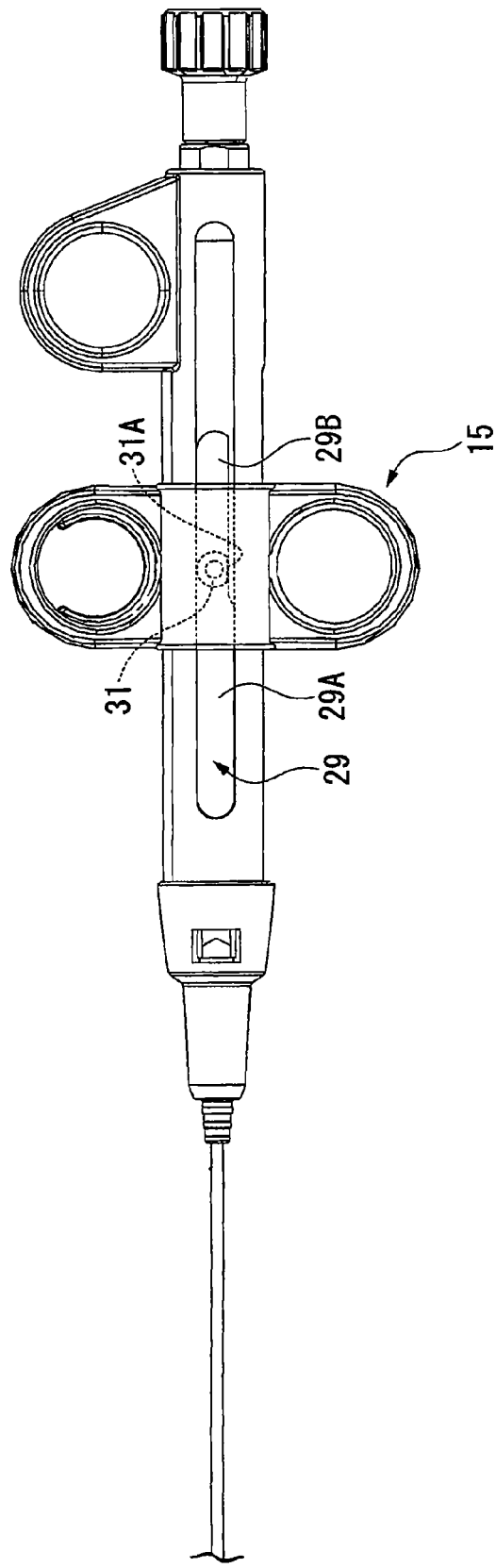
FIG. 17 shows the state in which the sliding portion is allowed to move to a second region of the groove.

When performing suturing manipulation, the user rotates the screw 30 so that the index line 30A is substantially parallel to the axial direction of the slider 15. Then, as shown in FIG. 17, since the shaft 31 is moved so that the flat portion 31A of the shaft 31 is substantially parallel to the longitudinal direction of the groove 29, and the length of the shaft 31 in the width direction of the groove 29 becomes smaller, thereby allowing the shaft 31 to enter the second region 29B of the groove 29. After operating the screw 30, the user retracts the slider 15 with respect to the operating portion main body 12, and moves the slider 15 to the second region 29B.

Then, the suture thread 104 of the suture unit 103 that is tied to the wire 5 is also received in the first sheath 8, and the stopper 105 abuts to the distal end of the first sheath 8. When the user retracts the slider 15 again, only the suture thread 104 is received in the first sheath 8 in a state that the stopper 105 is abutted to the first sheath 8. As a result, the distance between the stopper 105 and each of the anchors 106 and 107 decreases.

Figure 18:
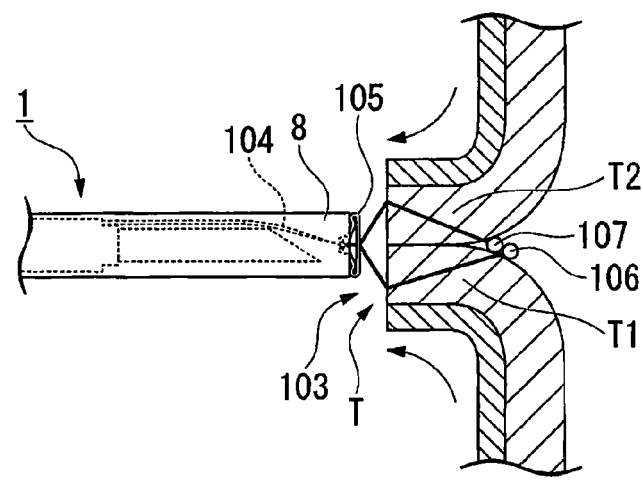
FIG. 18 shows tightening and suturing operation by the suturing device.

Since the anchors 106 and 107 are locked at the tissues T1 and T2, respectively, as shown in FIG. 18, the tissues T1 and T2 are pulled toward the suturing device 1 along with the anchors 106 and 107 as the stopper 105 approaches the anchors 106 and 107, and are brought into close contact with each other In this way, a suturing operation is performed on the target tissue T.

In this case, when the suture thread 104 is moved toward the mid-point portion 104A so as to be received in the first sheath 8, the engagement between the end portions 105A and 105B of the stopper 105 becomes loose. However, if the user tries to move the suture thread 104 toward the anchors 106 and 107, the movement in that direction is not allowed because the end portions 105A and 105B are more tightly engaged by the force applied to the suture thread 104. That is, because the stopper 105 is only allowed to move toward the anchors 106 and 107 and movement in an opposite direction is not allowed, the suture state of the target tissue T is not loosened or released.

Figure 19:
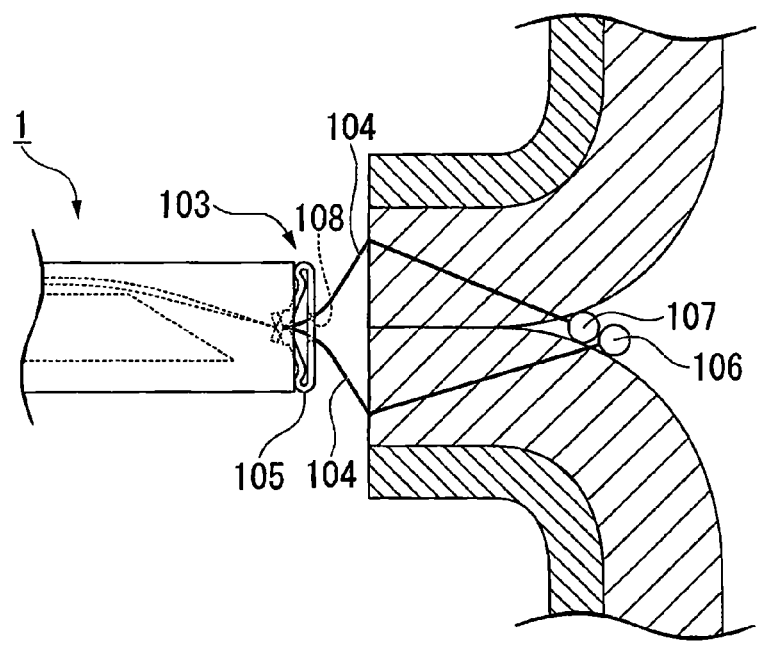
FIG. 19 is a partial enlarged view of the suture unit in the tightening and suturing operation.
Figure 20:
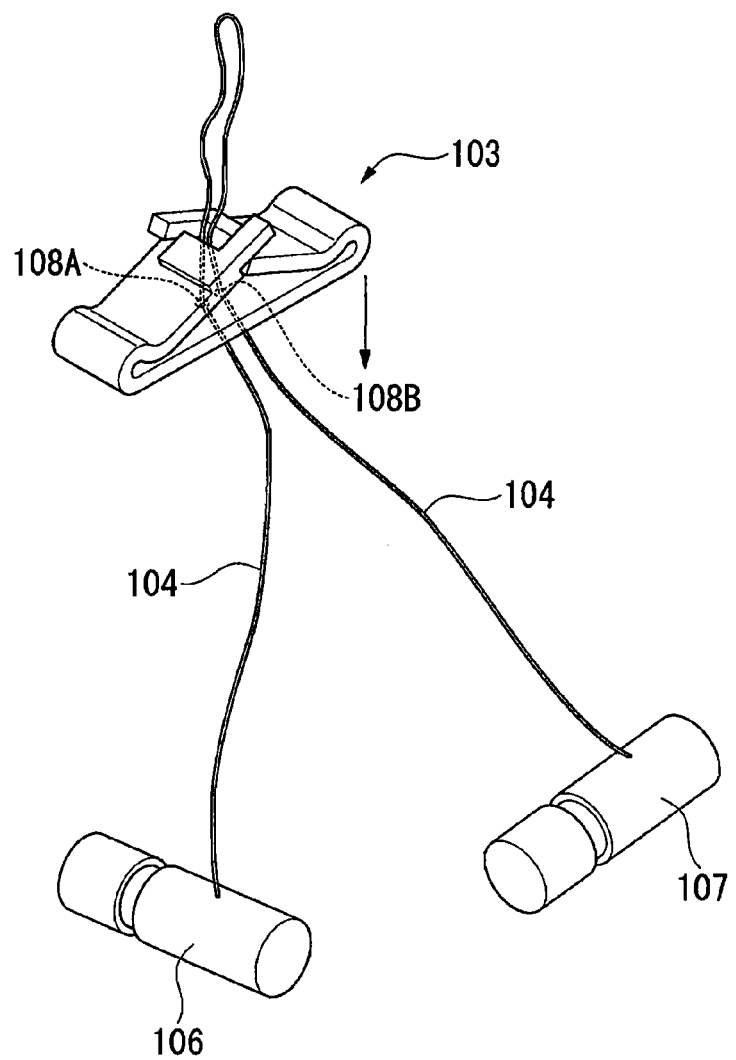
FIG. 20 shows a suture unit of a suturing device according to a modified example of the present invention.

Furthermore, the insertion hole 108 provided in the stopper 105 extends in the longitudinal direction of the stopper 105. Therefore, as the anchors 106 and 107 approach the stopper 105, as shown in FIG. 19, both ends of the suture thread 104 to which the anchors 106 and 107 are connected, are drawn so as to be separated from each other such that both end portions of the suture thread 104 are moved to both ends of the insertion hole 108, respectively. As a result, the stopper 105 rotates so as to be always positioned substantially parallel to a line connecting the first anchor 106 with the second anchor 107. That is, the stopper 105 is adjusted to be disposed in a direction substantially orthogonal to the extending direction of a laceration or the like to be sutured, thereby preventing the stopper 105 from burying into the interior of the laceration or the like.

When the suturing operation is completed, the user pulls the second rod 28 to retract the wire 5 with respect to the tube 7. When the distal end of the wire 5 is moved so as to be located on the rear side of the connection tube 11, the suture thread 104 comes off from the wire S and the suture unit 103 is separated from the suturing device 1. In this way, a series of treatments is completed.

According to the suturing device 1 of the present embodiment, since the slider control portion 16 is provided in the sliding portion 13 which advances and retracts the needle 4, the movement of the sliding portion 13 in the forward and backward direction is not allowed unless the control by the slider control portion 16 is deactivated. Therefore, it is possible to prevent an undesired movement of the sliding portion 13 in the forward and backward direction at the time of releasing the anchors 106 and 107 of the suture unit 103 by the release portion 14, and therefore it is possible to perform the suturing manipulation securely.

Furthermore, since the pressing portion 26 for deactivating the control by the slider control portion 16 protrudes to the inside of the ring 18A of the handle portion 18, only by hooking fingers into the ring 18A to push the slider 15 in a direction in which the user wants to move the sliding portion, the pressing portion 26 is pushed to deactivate the control by the slider control portion 16. Therefore, there is no need to perform an extra manipulation in order to deactivate the control, and only by operating a slider as usual, it is possible to perform the advancing and retracting manipulation of the sliding portion 13 while deactivating the control by the slider control portion 16.

Furthermore, the shaft 31 of the screw 30 attached to the slider 15 is formed in a D-shape and is engaged with the groove 29 having the first and second regions 29A and 29B which have different widths. Therefore, by adjusting the orientation of the flat portion 31A, the slidably movable range of the slider 15 in the groove 29 is adjusted; thereby, preventing the slider 15 from retracting more than necessary. When performing a manipulation such as tightening the tissues, by rotating the screw 30 to adjust the orientation of the flat portion 31A, the slider 15 is allowed to retract greatly. Furthermore, since the index line 30A is provided in the screw 30, it is possible to easily recognize the orientation of the flat portion 31A.

In addition, the insertion hole 108 which extends in the longitudinal direction of the stopper 105 is provided in the stopper 105 of the suture unit 103. Therefore, when moving the stopper 105 to the anchors 106 and 107 to perform a manipulation such as tightening and suturing the tissues, both ends of the suture thread 104 to which the anchors 106 and 107 are connected, are drawn so as to be separated from each other such that both end portions of the suture thread 104 are moved to the both ends of the insertion hole 108, respectively.

Generally, the anchors 106 and 107 are locked to the tissues oppose to each other with a laceration or the like disposed therebetween, so that a line connecting the first anchor 106 with the second anchor 107 is substantially orthogonal to the longitudinal direction of the laceration or the like as a suturing target. As a result, when the suture thread 104 moves as described above, the orientation of the stopper 105 is adjusted to be substantially orthogonal to a direction in which the laceration or the like extends. Therefore, it is possible to prevent the stopper 105 from becoming parallel to the extending direction of the laceration or the like, and it is possible to prevent the stopper 105 from burying into the interior of the laceration or the like even when the tissues are strongly tightened. Accordingly, the user can visually confirm the position or the like of the stopper 105 securely even after the manipulation, and can perform a follow-up manipulation or the like adequately, if necessary.

Hereinabove, although a preferred embodiment of the present invention has been described and illustrated, the present invention is not limited to this embodiment. Additions, omissions, substitutions, and other modifications can be made to the configurations described and illustrated above without departing from the scope and spirit of the present invention.

For example, in the embodiment described above, the description has been made for the case in which the insertion hole formed in the stopper of the suture unit is an elliptical hole extending in the longitudinal direction of the stopper. Instead of this, as a modified example shown in FIG. 20, two insertion holes 108A and 108B aligning in the longitudinal direction of the stopper 105 may be formed, and the end portions of the suture thread 104 to which the anchors 106 and 107 are connected may be inserted into the insertion holes. In this case, similar to the above-described embodiment, it is also possible to suitably adjust the orientation of the stopper with respect to the extending direction of the laceration or the like to as a suturing target.

In addition, although in the embodiments described above, the description has been made for the case in which, in the slider control portion 16, the pair of the plate clutches 19 and the pair of the biasing members 20 are used for controlling the sliding movement of the sliding portion in the forward and backward direction, other constructions may be adopted. For example, a slider control portion may be constructed so as to control the sliding movement of the sliding portion in only one direction. In this case, one plate clutch and one biasing member may be provided in a slider control portion such that the sliding movement only in the forward direction is controlled so as to prevent the needle from protruding extremely. In this case, other known one-way clutch or the like may be employed in the slide control portion.

In addition, in the embodiment described above, the description has been made for the case in which the shaft 31 of the screw 30 engaged with the groove 29 of the operating portion main body 12 is formed in a D-shape having one flat portion 31A. Instead of this, a second flat portion may be provided such that the second flat portion is substantially parallel to the flat portion 31A with a center of the shaft 31 disposed therebetween. In this case, when performing a manipulation for allowing the slider 15 to move to the second region 29B of the groove 29, it is possible to securely adjust the slidably movable range of the slider only by making the index line 30A parallel to the axis of the slider 15 without considering the position of the flat portion 31A.

It should be noted that the scope of the present invention is to be defined by the claims appended hereto rather than being limited to the descriptions presented above.

What is claimed is:

1. A suturing device that sutures tissues within a body cavity by releasing a suture unit, the suturing device comprising:
    a first anchor and a second anchor included in the suture unit;
    a hollow needle which receives the first anchor and the second anchor inside of the needle;
    a tube which is fixed to a proximal end side of the needle;
    a wire inserted into the tube and the needle;
    a first sheath through which the tube and the needle are inserted;
    an operating portion main body fixed to a proximal end of the first sheath;
    a slider fixed to a proximal end of the tube and configured to move forward and backward freely in a sliding manner with respect to the operating portion main body;
    a slider control portion configured to regulate movement of the slider with respect to the operating portion main body at all times;
    a pair of rings which are provided in the slider when a press force is applied to the slider by a user hooking the user's fingers into the pair of rings, an operation to allow the slider move forward and backward in a sliding manner with respect to the operating portion main body is performed; and
    a deactivation member which is disposed in a position where the deactivation member is capable of being pressed along with the pair of rings when an operation is performed to allow the deactivation member to deactivate the regulation of the slider control portion by the user applying a press force to the pair of rings; wherein
    when the slider is retracted by the user in a backward direction with respect to the operating portion main body, the needle is received in the first sheath; and
    when the slider is protruded by the user in a forward direction with respect to the operating portion main body, the needle is exposed from a distal end of the first sheath, wherein:
    the sliding portion further comprises a shaft inserted so as to be parallel to the advancing and retracting direction with respect to the slider;
    a pair of plate clutches, each plate clutch having a first end portion having a through-hole through which the shaft is inserted, and a second end portion engaged with the slider; and
    a biasing member biasing the first end portions of the pair of the plate clutches so that the first end portions are separated from each other in the advancing and retracting direction;
    an inner diameter of the through-hole is set greater than an outer diameter of the shaft; and
    the second end portions of the pair of the plate clutches are positioned between the first end portions in the advancing and retracting direction in the normal state.

2. The suturing device according to claim 1, wherein:
    the slider control portion includes the deactivation member having an abutting portion configured to abut the first end portion of the pair of the plate clutches; and
    by operating the deactivation member, the abutting portion abuts the first end portion of one of the pair of the plate clutches and moves against the biasing force of the biasing member such that the position of the one first end portion of the one clutch becomes the same as the second end portion of the one clutch thereby deactivating the control.

3. The suturing device according to claim 2, wherein:
    a handle portion is provided with the pair of rings for hooking fingers; and
    a pressing portion of the deactivation member is formed such that when the deactivation member is not pressed by the user, a part of the pressing portion that is capable of being pressed protrudes inside of one of the pair of rings.

* * * * *